United States Patent
Shen et al.

(10) Patent No.: US 11,420,991 B2
(45) Date of Patent: Aug. 23, 2022

(54) CONFINED PORPHYRIN CO(II) AND PREPARATION METHOD AND APPLICATION THEREOF

(71) Applicant: Zhejiang University of Technology, Hangzhou (CN)

(72) Inventors: Haimin Shen, Hangzhou (CN); Lei Ning, Hangzhou (CN); Yuanbin She, Hangzhou (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 157 days.

(21) Appl. No.: 16/928,522

(22) Filed: Jul. 14, 2020

(65) Prior Publication Data
US 2021/0155650 A1 May 27, 2021

(30) Foreign Application Priority Data

Nov. 25, 2019 (CN) .......................... 201911161924.9

(51) Int. Cl.
*C07F 15/06* (2006.01)
*B01J 31/18* (2006.01)

(52) U.S. Cl.
CPC ......... *C07F 15/065* (2013.01); *B01J 31/1815* (2013.01); *B01J 2231/70* (2013.01); *B01J 2531/845* (2013.01)

(58) Field of Classification Search
CPC .. C07F 15/065; B01J 31/1815; B01J 2231/70; B01J 2531/845
See application file for complete search history.

(56) References Cited

U.S. PATENT DOCUMENTS

| | | | | | |
|---|---|---|---|---|---|
| 5,723,697 | A | * | 3/1998 | Bhinde | C07C 29/50 568/910.5 |
| 5,760,216 | A | * | 6/1998 | Chorghade | C07D 405/04 534/10 |
| 5,817,830 | A | * | 10/1998 | Therien | C07D 207/33 548/400 |
| 6,117,369 | A | * | 9/2000 | Shelnutt | G11B 7/248 252/582 |
| 6,124,452 | A | * | 9/2000 | DiMagno | C07D 487/22 540/145 |
| 7,632,942 | B2 | * | 12/2009 | Ishida | C07C 29/50 568/835 |
| 2004/0157281 | A1 | * | 8/2004 | Hulkower | G01N 33/581 435/7.92 |
| 2016/0303553 | A1 | * | 10/2016 | Chorghade | C07F 15/025 |

FOREIGN PATENT DOCUMENTS

| | | |
|---|---|---|
| CN | 108864082 A | 11/2018 |
| CN | 109180556 A | 1/2019 |
| WO | 2019/030294 A | 2/2019 |
| WO | 2019/046316 A1 | 7/2019 |
| WO | 2019/069911 A1 | 11/2019 |

OTHER PUBLICATIONS

F. D'Souza et al., "Electron Transfer Processes of β-Pyrrole Brominated Porphyrins: Structural vs. Electronic Effects." N4-Macrocyclic Metal Complexes (Springer) 439-466 (2006) (Year: 2006).*
W. Su et al., Proceedings of SPIE, Structure-optical property relationships of porphyrins (1998) (Year: 1998).*
N. Nelson et al., Chem. Commun., 2071-2072 (1999) (Year: 1999).*
R. George et al., 24 Polyhedron, 679-684 (2005) (Year: 2005).*
R. George et al., 28 Transition Metal Chemistry, 858-863 (2003) (Year: 2003).*
R. George et al., 22 Polyhedron, 3145-3154 (2003) (Year: 2003).*
F. D'Souza et al., 32 Inorganic Chemistry, 4042-4048 (1993) (Year: 1993).*
P. Bhyrappa et al., 30 Inorganic Chemistry, 239-245 (1991) (Year: 1991).*
Alsheri et al., New Catalysts with dual-functionality for cyclohexane selective oxidation, Applied Catalysis A, General 554 (2018) 71-79.
Xiang et al., Heteroatom-induced band-reconstruction of metal vanadates for photocatalytic cyclohexane oxidation towards KA-oil selectivity, Applied Catalysis A, General 575 (2019) 120-131.

(Continued)

Primary Examiner — Alexander R Pagano
(74) Attorney, Agent, or Firm — Thomas | Horstemeyer, LLP

(57) ABSTRACT

A confined porphyrin Co(II), which is prepared by the following method: Equimolar amounts of aromatic aldehyde and pyrrole are condensed under acidic conditions to synthesize phenyl porphyrin compounds; the phenyl porphyrin compounds are metallized in a chloroform-methanol solution to obtain porphyrin Cu(II), which is brominated and demetallized to obtain confined porphyrin; the confined porphyrin is stirred and refluxed in a methanol solution for 12.0-24.0 h to obtain confined porphyrin Co(II). Its application is as follows: The confined porphyrin Co(II) is dissolved in cycloalkanes; the reaction system is sealed, and heated to 100 to 130° C. with stirring, to which oxygen is introduced to 0.2 to 3.0 MPa; the reaction is carried out for 3.0 to 24.0 h with stirring with the set temperature and oxygen pressure being maintained; and then the reaction solution is subjected to post-treatment to obtain the products.

9 Claims, 1 Drawing Sheet

(56) References Cited

OTHER PUBLICATIONS

Wan et al., Efficient and selective photocatalytic oxidation of cyclohexane using O2 as oxidant in VOCl2 solution and mechanism insight, Chemical Engineering Science 203 (2019) 163-172.

Pamin et al., Three Generations of Cobalt Porphyrins as Catalysts in the Oxidation of Cycloalkanes, ChemsusChem 2019, 12, 684-691.

Xu et al., Copolymeric Schiff Base Cu: A Platform for Active and Recyclable Catalyst in Aerobic Oxidations, Ind. Eng. Chem. Res. 2017, 56, 15030-15037.

Antonangelo et al., Highly active manganese porphyrin-based microporous network polymers for selective oxidation reactions, Journal of Catalysis 369 (2019) 133-142.

Kim et al., Discovery of Potent, Selective, and Orally Bioavailable Estrogen-Related Receptor-γ Inverse Agonists to Restore the Sodium Iodide Symporter Function in Anaplastic Thyroid Cancer, J. Med. Chem. 2019, 62, 1837-1858.

Huang et al., Systematic Engineering of Single Substitution in Zirconium Metal-Organic Frameworks toward High-Performance Catalysis, J. Am. Chem. Soc. 2017, 139, 18590-18597.

Yao et al., A convenient, high-yielding, chromatography-free method for the insertion of transition metal acetates into porphyrins, Polyhedron 58 (2013) 2-6.

Guimaraes et al., An eco-friendly approach to the cyclohexane oxidation catalyzed by manganese porphyrins: Green and solvent free systems, Polyhedron 163 (2019) 144-152.

Sniechowska et al., Structure and dynamics processes in free-base chlorins controlled by chemical modifications of macroring and aryl groups in meso-positions, RSC Adv., 2017, 7, 24795-24805.

Yang et al., Catalytically active Au—O(OH)x species stabilized by alkali ions on zeolites and mesoporous oxides, Sciencemag.org, Dec. 19, 2014, vol. 346, Issue 6216, 1498.

Hwang et al., One-pot room-temperature conversion of cyclohexane to adipic acid by ozone and UV light, Sciencemag.org, Dec. 19, 2014, vol. 346 Issue 6216, 1495-1497.

\* cited by examiner

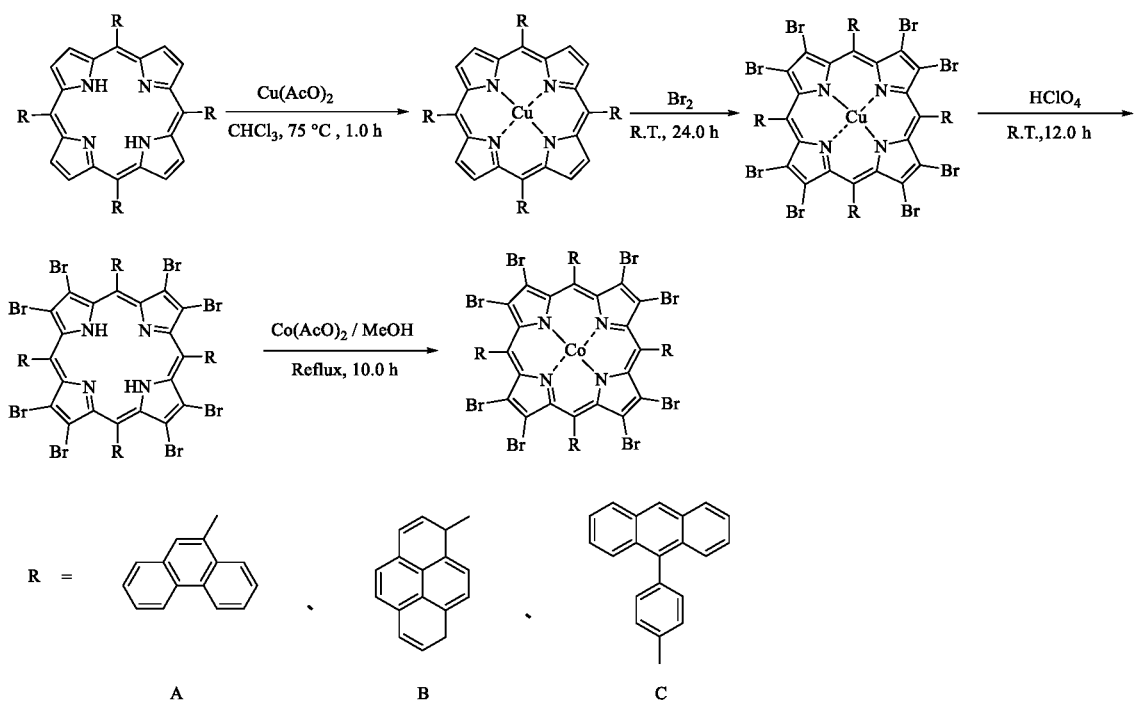

CONFINED PORPHYRIN CO(II) AND PREPARATION METHOD AND APPLICATION THEREOF

CROSS-REFERENCE TO RELATED APPLICATIONS

This application claims priority to, and the benefit of, CN Patent Application No. 201911161924.9, filed Nov. 25, 2019, which is herein incorporated by reference in its entirety.

TECHNICAL FIELD

The disclosure relates to a confined porphyrin Co(II), preparation method thereof and application thereof in oxidation of cycloalkanes by molecular oxygen, and pertains to the field of organic catalysis and fine organic synthesis.

BACKGROUND

Catalytic oxidation of cycloalkanes is an important chemical conversion process. The oxidation products thereof, cycloalkanols and cycloalkanones, are not only important organic solvents, but also important fine chemical intermediates, which are widely used for the synthesis of fine chemical products such as pesticides, pharmaceuticals, dyes and the like. Synthesis (WO 2019046316; WO 2019030294; WO 2019069911; CN 108864082; CN 109180556; Journal of Medicinal Chemistry 2019, 62: 1837-1858; Russian Journal of General Chemistry 2018, 88: 2646-2652). In addition, cycloalkanols and cycloalkanones can be further oxidized to prepare aliphatic diacids, which are important precursors for the preparation of various polymer materials, e.g., catalytic oxidation of cyclohexane mainly results in products, cyclohexanols and cyclohexanones, which are further oxidized to adipic acid, an important precursor for producing nylon-66 and nylon-6, and there is a large market demand (Applied Catalysis A, General 2019, 575: 120-131; Chemical Engineering Science 2019, 203: 163-172; Catalysis A, General 2018, 554: 71-79; Industrial & Engineering Chemistry Research 2017, 56: 15030-15037). At present, catalytic oxidation of cycloalkanes in industry is mainly achieved by using homogeneous cobalt(II) salt or manganese (II) salt as the catalyst, and molecular oxygen or air as the oxidant, at 130 to 160° C., and a pressure of 0.80 to 3.0 MPa (Applied Catalysis A, General 2019, 575: 120-131; Science 2014, 346: 1495-1498). Due to the high reaction temperature, the generated cycloalkanols and cycloalkanones are prone to be deeply oxidized to produce aliphatic diacids. Although cycloalkanols and cycloalkanones are raw materials for the preparation of aliphatic diacids, the generation of aliphatic diacids during the production of cycloalkanols and cycloalkanones is a problem to be avoided. The formation of aliphatic diacids blocks the pipelines for catalytic oxidation of cycloalkanes, which is not conducive to continuous production. Therefore, there is an urgent need in industry of catalytic cycloalkane oxidation for developing a new method for selective catalytic oxidation of cycloalkanes, maximizing the selectivity of cycloalkanols and cycloalkanones on the premise of ensuring the conversion of cycloalkanes, and reducing and avoiding the formation of aliphatic diacids. This has a great production and application value, and also has an important theoretical research value.

Metalloporphyrin, as a model compound of cytochrome P-450, is widely used in biomimetic catalysis of various organic synthesis reactions, especially oxidation reactions (ChemSusChem 2019, 12: 684-691; Polyhedron 2019, 163: 144-152; Journal of Catalysis 2019, 369: 133-142). Metalloporphyrin has a nearly planar molecular structure, which enables the catalytically active metal center to be exposed to the catalytic system to the maximum extent. As a preferred catalyst for catalytic oxidation of cycloalkanes, it can exhibit an excellent catalytic activity in an amount that is $1/1000000$ to $1/100000$ of the amount of the substrate, and can significantly reduce the costs of catalytic oxidation of cycloalkanes (ChemSusChem 2019, 12: 684-691; Polyhedron 2019, 163: 144-152; Journal of Catalysis 2019, 369: 133-142). Although metalloporphyrin, as a catalyst, has the advantages of low catalyst dosage, high catalytic efficiency, easy structure adjustment, good biocompatibility, and being green and environmentally friendly, it still cannot reduce and avoid the formation of aliphatic diacids in the process of catalytic oxidation of cycloalkanes to cycloalkanols and cycloalkanones by molecular oxygen.

SUMMARY

In order to reduce or avoid the formation of aliphatic diacids during the catalytic oxidation of cycloalkanes, the object of this disclosure is to provide a confined porphyrin Co(II) and preparation method thereof, and application method thereof in oxidation of cycloalkanes by molecular oxygen. In this disclosure, the structure of porphyrin Co(II) is optimized, and it is subjected to bromination treatment to synthesize the confined porphyrin Co(II). Compared with traditional porphyrins, the confined porphyrin Co(II) has substituents with larger space volume, forms a confined space environment, and restricts the escape of cycloalkyl radicals from the solvent cage, which allows for a smooth spring-back of hydroxyl radicals generated by the catalytic center to the cycloalkyl radicals, thereby producing cycloalkyl alcohols. In addition, bromination of the porphyrin ring enhances the stability of the porphyrin structure, provides better metal catalytic active centers, which not only significantly improves the selectivity of cycloalkanols and cycloalkanones, but also increases the conversion of cycloalkanes, suppresses the formation of aliphatic diacids during the oxidation of cycloalkanes, which is conducive to continuous production in industrialization.

The technical solution of this disclosure is as follows:

A confined porphyrin Co(II) having the following structure:

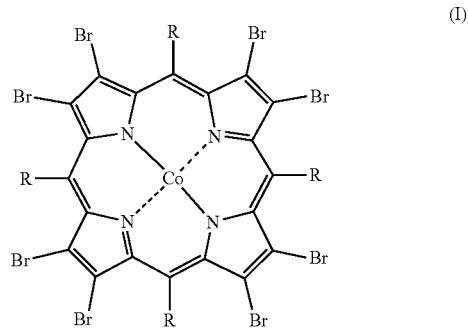

(I)

-continued

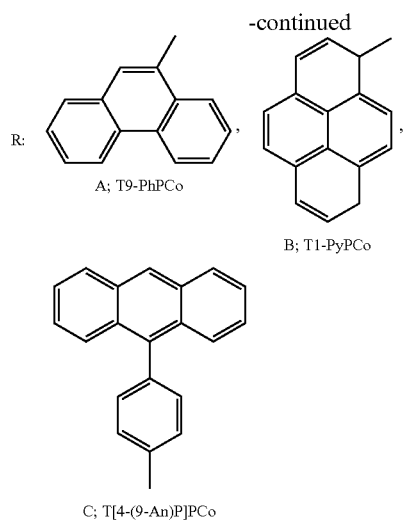

A; T9-PhPCo

B; T1-PyPCo

C; T[4-(9-An)P]PCo

A method for preparing a confined porphyrin Co(II), which is described as follows:

Equimolar amounts of aromatic aldehyde and pyrrole are condensed under acidic conditions to synthesize phenyl porphyrin compounds; porphyrin and anhydrous copper (II) acetate are stirred at reflux in chloroform for 3.0-8.0 h, filtered with suction, and desolventized under reduced pressure to obtain porphyrin Cu(II); in chloroform, the porphyrin Cu(II) and liquid bromine are stirred at room temperature for 24.0-36.0 h, which is quenched with a saturated sodium thiosulfate solution after the completion of reaction, wherein liquid separation is performed by extraction with chloroform and water, and the organic phase in the lower layer is dried over anhydrous sodium sulfate, filtered with suction, and desolventized under reduced pressure to obtain confined porphyrin Cu(II); the confined porphyrin Cu(II) and perchloric acid are stirred at room temperature for 12.0-24.0 h using chloroform as the solvent, and neutralized with a saturated sodium bicarbonate solution, wherein liquid separation is performed by extraction with chloroform and water, and the organic phase in the lower layer is dried over anhydrous sodium sulfate, filtered with suction, and desolventized under reduced pressure to obtain confined porphyrin; the confined porphyrin and a methanol solution of anhydrous cobalt(II) acetate are stirred at reflux for 12.0-24.0 h using chloroform as the solvent, wherein liquid separation is performed by extraction with chloroform and water, and the organic phase in the lower layer is dried over anhydrous sodium sulfate, filtered with suction, desolventized under reduced pressure, and vacuum-dried at 60 to 150° C. for 8.0 to 36.0 h to obtain the confined porphyrin Co(II).

Further, the ratio of the amount of substance of porphyrin Cu(II) to liquid bromine is 1:(500 to 10);

The ratio of the amount of substance of the confined porphyrin Cu(II) to perchloric acid is 1:(2000 to 200);

The ratio of the amount of substance of the confined porphyrin to anhydrous cobalt(II) acetate is 1:(100 to 5).

In the method for the preparation of a confined porphyrin Co(II) according to this disclosure, the perchloric acid is a generally commercially available perchloric acid, wherein the concentration of $HClO_4$ is 70 to 72 wt %.

In this disclosure, the terms "A", "B", and "C" have no special meaning, and are only codes for different substances.

The invention provides a use of the confined porphyrin Co(II) for catalyzing the selective oxidation of cycloalkanes by molecular oxygen.

The use is carried out by the following process: The confined porphyrin Co(II) is dispersed in cycloalkanes; the reaction system is sealed, and heated to 100 to 130° C. with stirring; oxygen is introduced to 0.2 to 3.0 MPa; the reaction is carried out for 3.0 to 24.0 h with stirring with the set temperature and oxygen pressure being maintained; and then the reaction solution is subjected to post-treatment to obtain the products cycloalkanols and cycloalkanones;

The ratio of the amount of substance of the porphyrin Co(II) to cycloalkane is 1:(1000000 to 500), preferably 1:(100000 to 1000);

The stirring rate is 100 to 1500 rpm, preferably 600 to 1200 rpm;

The reaction temperature is 100 to 130° C.;

The reaction pressure is 0.2 to 3.0 MPa;

The reaction time is 3.0 to 24.0 h;

The post-treatment method is as follows: After the reaction is completed, triphenylphosphine ($PPh_3$, the amount of which is 2.5 to 25% of the amount of cycloalkanes) is added to the reaction solution, and stirred at room temperature (20 to 30° C.) for 30 min to reduce the generated peroxides, and the crude product is subjected to distillation, distillation under reduced pressure and recrystallization to obtain the oxidation product.

In this disclosure, the cycloalkane is selected from cyclopentane, cyclohexane, cycloheptane, cyclooctane, cyclononane, cyclodecane, cycloundecane, cyclododecane, or a mixture of two or more thereof in a random ratio;

The confined porphyrin Co(II) is selected from the compounds represented by formula (I), or a mixture of two or more thereof in a random ratio, and the compounds are A: 5,10,15,20-tetra(9-phenanthryl)-2,3,7,8,12,13,17,18-octabromoporphyrin cobalt(II), B: 5,10,15,20-tetra(1-pyrenyl)-2,3,7,8,12,13,17,18-octabromoporphyrin cobalt(II), and C: 5,10,15,20-tetra[4-(9-anthryl)-phenyl)]-2,3,7,8,12,13,17,18-octabromoporphyrin cobalt(II), respectively.

The porphyrin Co(II) used in the comparative experiment of this disclosure is selected from the compounds represented by formula (II), or a mixture of two or more thereof in a random ratio:

(II)

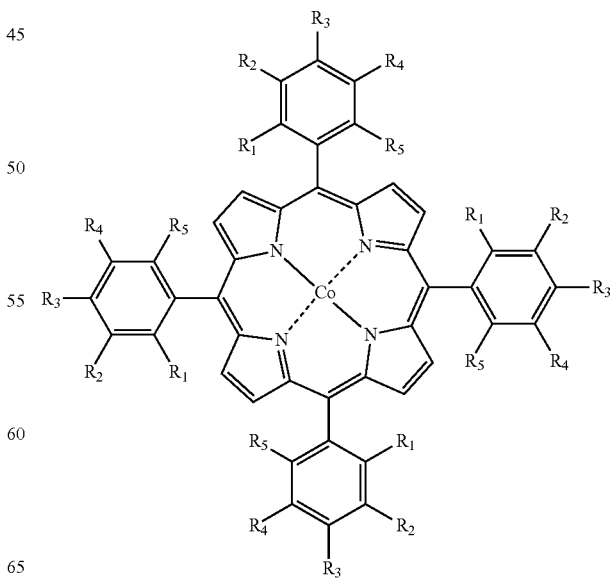

In formula (II), $R_1$, $R_2$, $R_3$, $R_4$, and $R_5$ are each independently: hydrogen, methyl, ethyl, propyl, butyl, isopropyl, tert-butyl, phenyl, 1-naphthyl, 2-naphthyl, methoxy, ethoxy, hydroxyl, mercapto, amino, methylamino, ethylamino, dimethylamino, 1-hydroxyethyl, nitro, cyano, carboxyl, benzyl, fluoro, chloro, bromo or iodo.

The beneficial effects of this disclosure are mainly shown in: In this disclosure, a confined porphyrin Co(II) is prepared, and used for catalyzing the selective oxidation of cycloalkanes by molecular oxygen to produce cycloalkanols and cycloalkanones, which has high selectivity for cycloalkanols and cycloalkanones and effectively suppresses the formation of aliphatic diacids; the catalyst is characterized by good stability, low costs of cycloalkanol and cycloalkanone synthesis, and low selectivity for aliphatic diacids, which is conducive to the continuation of cycloalkane oxidation process and the separation of products; there is a potential to solve the problem in industry that cycloalkanols and cycloalkanones are easy to be deeply oxidized to produce aliphatic diacids in the process of catalytic oxidation of cycloalkanes; the disclosure is an efficient and feasible new method for selectively catalytic oxidation of cycloalkanes.

BRIEF DESCRIPTION OF THE DRAWINGS

FIG. 1 is a flow chart of the preparation method of confined porphyrin Co(II).

DESCRIPTION OF THE EMBODIMENTS

This disclosure will be further described by the following specific embodiments, but the scope of protection of this disclosure is not limited thereto.

Examples 1-13 are the synthesis of the confined porphyrin Co(II);

Examples 14-39 are the use of the confined porphyrin Co(II) in the catalytic oxidation of cycloalkanes by molecular oxygen;

The porphyrin Cu(II) used in this disclosure is synthesized by referring to Journal of the American Chemical Society 2017, 139(51), 18590-18597; RSC Advances 2017, 7(40), 24795-24805; Polyhedron 2013, 58, 2-6.

The reagents used in this disclosure are all commercially available, analytically pure.

Example 1

In a 500 mL three-neck round-bottom flask, 20.6241 g (100 mmol) of 9-formaldehyde phenanthrene is dissolved in 300 mL of propionic acid, stirred and heated to reflux for 10 min under the protection of $N_2$; 6.7812 g (100 mmol) of freshly distilled pyrrole is added dropwise, reacted for 2.0 h, cooled to room temperature, filtered with suction, recrystallized with methanol, and dried to obtain 5.0710 g of porphyrin T9-PhP, with a yield of 20%; in a 250 mL single-neck round-bottom flask, 1.0152 g (1.0 mmol) of T9-PhP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.8858 g of T9-PhPCu(II), with a yield of 80%; in a 500 mL single-neck round-bottom flask, 0.5401 g (0.5 mmol) of T9-PhPCu(II) is dissolved in 150 mL of chloroform, to which 5.3 mL (100 mmol) of $Br_2$ is titrated at constant pressure, stirred at room temperature for 24.0 h, quenched with the addition of 3.1600 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.4142 g of dark green solids, T9-PhPBr$_8$Cu(II), with a yield 48.5%; in a 250 mL single-neck round-bottom flask, 0.3416 g (0.2 mmol) of T9-PhPBr$_8$Cu(II) is dissolved in 100 mL of chloroform, to which 15 mL (180 mmol) of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2410 g of dark green solids, T9-PhPBr$_8$, with a yield of 73.1%; in a 250 mL single-neck round-bottom flask, 0.1652 g (0.1 mmol) of T9-PhPBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1167 g of reddish brown solids, T9-PhPBr$_8$Co(II), with a yield of is 68.5%.

Example 2

In a 500 mL three-neck round-bottom flask, 20.6241 g (100 mmol) of 9-formaldehyde phenanthrene is dissolved in 300 mL of propionic acid, stirred and heated to reflux for 10 min under the protection of $N_2$; 6.7812 g (100 mmol) of freshly distilled pyrrole is added dropwise, reacted for 2.0 h, cooled to room temperature, filtered with suction, recrystallized with methanol, and dried to obtain 5.0710 g of porphyrin T9-PhP, with a yield of 20%; in a 250 mL single-neck round-bottom flask, 1.0152 g (1.0 mmol) of T9-PhP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.8858 g of T9-PhPCu(II), with a yield of 80%; in a 500 mL single-neck round-bottom flask, 0.5401 g (0.5 mmol) of T9-PhPCu(II) is dissolved in 150 mL of chloroform, to which 0.3 mL (5 mmol) of $Br_2$ is titrated at constant pressure, stirred at room temperature for 24.0 h, quenched with the addition of 1.584 g (10 mmol) of sodium thiosulfate (dissolved in 50 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.3612 g of dark green solids, T9-PhPBr$_8$Cu(II), with a yield 42.3%; in a 250 mL single-neck round-bottom flask, 0.3416 g (0.2 mmol) of T9-PhPBr$_8$Cu(II) is dissolved in 100 mL of chloroform, to which 15 mL of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2410 g of dark green solids, T9-PhPBr$_8$, with a yield of 73.1%; in a 250 mL single-neck round-bottom flask, 0.1652 g (0.1 mmol) of T9-PhPBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1167 g of reddish brown solids, T9-PhPBr$_8$Co(II), with a yield of is 68.5%.

Example 3

In a 500 mL three-neck round-bottom flask, 20.6241 g (100 mmol) of 9-formaldehyde phenanthrene is dissolved in 300 mL of propionic acid, stirred and heated to reflux for 10 min under the protection of N$_2$; 6.7812 g (100 mmol) of freshly distilled pyrrole is added dropwise, reacted for 2.0 h, cooled to room temperature, filtered with suction, recrystallized with methanol, and dried to obtain 5.0710 g of porphyrin T9-PhP, with a yield of 20%; in a 250 mL single-neck round-bottom flask, 1.0152 g (1.0 mmol) of T9-PhP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.8858 g of T9-PhPCu(II), with a yield of 80%; in a 500 mL single-neck round-bottom flask, 0.5401 g (0.5 mmol) of T9-PhPCu(II) is dissolved in 150 mL of chloroform, to which 13.3 mL (250 mmol) of Br$_2$ is titrated at constant pressure, stirred at room temperature for 24.0 h, quenched with the addition of 6.321 g (40 mmol) of sodium thiosulfate (dissolved in 200 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.4364 g of dark green solids, T9-PhPBr$_8$Cu(II), with a yield 51.1%; in a 250 mL single-neck round-bottom flask, 0.3416 g (0.2 mmol) of T9-PhPBr$_8$Cu(II) is dissolved in 100 mL of chloroform, to which 15 mL of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2410 g of dark green solids, T9-PhPBr$_8$, with a yield of 73.1%; in a 250 mL single-neck round-bottom flask, 0.1652 g (0.1 mmol) of T9-PhPBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1167 g of reddish brown solids, T9-PhPBr$_8$Co(II), with a yield of is 68.5%.

Example 4

In a 500 mL three-neck round-bottom flask, 20.6241 g (100 mmol) of 9-formaldehyde phenanthrene is dissolved in 300 mL of propionic acid, stirred and heated to reflux for 10 min under the protection of N$_2$; 6.7812 g (100 mmol) of freshly distilled pyrrole is added dropwise, reacted for 2.0 h, cooled to room temperature, filtered with suction, recrystallized with methanol, and dried to obtain 5.0710 g of porphyrin T9-PhP, with a yield of 20%; in a 250 mL single-neck round-bottom flask, 1.0152 g (1.0 mmol) of T9-PhP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.8858 g of T9-PhPCu(II), with a yield of 80%; in a 500 mL single-neck round-bottom flask, 0.5401 g (0.5 mmol) of T9-PhPCu(II) is dissolved in 150 mL of chloroform, to which 5.3 mL (100 mmol) of Br$_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.4142 g of dark green solids, T9-PhPBr$_8$Cu(II), with a yield 48.5%; in a 250 mL single-neck round-bottom flask, 0.3416 g (0.2 mmol) of T9-PhPBr$_8$Cu(II) is dissolved in 100 mL of chloroform, to which 32 mL (400 mmol) of perchloric acid is added, stirred at room temperature for 12.0 h, and washed with a saturated sodium bicarbonate solution (5×200 mL) to afford an organic phase in the lower layer which is a dark green solution, and which is dried over anhydrous sodium sulfate, filtered with suction, and desolventized under reduced pressure to obtain 0.2440 g of dark green solids, T9-PhPBr$_8$, with a yield of 74.1%; in a 250 mL single-neck round-bottom flask, 0.1652 g (0.1 mmol) of T9-PhPBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1167 g of reddish brown solids, T9-PhPBr$_8$Co(II), with a yield of is 68.5%.

Example 5

In a 500 mL three-neck round-bottom flask, 20.6241 g (100 mmol) of 9-formaldehyde phenanthrene is dissolved in 300 mL of propionic acid, stirred and heated to reflux for 10 min under the protection of N$_2$; 6.7812 g (100 mmol) of freshly distilled pyrrole is added dropwise, reacted for 2.0 h, cooled to room temperature, filtered with suction, recrystallized with methanol, and dried to obtain 5.0710 g of porphyrin T9-PhP, with a yield of 20%; in a 250 mL single-neck round-bottom flask, 1.0152 g (1.0 mmol) of T9-PhP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.8858 g of T9-PhPCu(II), with a yield of 80%; in a 500 mL single-neck round-bottom flask, 0.5401 g (0.5 mmol) of T9-PhPCu(II) is dissolved in 150 mL of chloroform, to which 5.3 mL (100 mmol) of Br$_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.4142 g of dark green solids, T9-PhPBr$_8$Cu(II), with a yield 48.5%; in a 250 mL single-neck round-bottom flask, 0.3416 g (0.2 mmol) of T9-PhPBr$_8$Cu(II) is dissolved in 100 mL of chloroform, to which 3 mL (40 mmol) of perchloric acid is added, stirred at room temperature for 12.0 h, and washed with a saturated sodium bicarbonate solution (5×50 mL) to afford an organic phase in the lower layer which is a dark green solution, and which is dried over anhydrous sodium sulfate, filtered with suction, and desolventized under reduced pressure to obtain 0.2381 g of dark green solids, T9-PhPBr$_8$, with a yield of 72.3%; in a 250 mL single-neck round-bottom flask, 0.1652 g (0.1 mmol) of T9-PhPBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1167 g of reddish brown solids, T9-PhPBr$_8$Co(II), with a yield of is 68.5%.

Example 6

In a 500 mL three-neck round-bottom flask, 20.6241 g (100 mmol) of 9-formaldehyde phenanthrene is dissolved in 300 mL of propionic acid, stirred and heated to reflux for 10 min under the protection of N$_2$; 6.7812 g (100 mmol) of freshly distilled pyrrole is added dropwise, reacted for 2.0 h, cooled to room temperature, filtered with suction, recrystallized with methanol, and dried to obtain 5.0710 g of porphyrin T9-PhP, with a yield of 20%; in a 250 mL single-neck round-bottom flask, 1.0152 g (1.0 mmol) of T9-PhP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.8858 g of T9-PhPCu(II), with a yield of 80%; in a 500 mL single-neck round-bottom flask, 0.5401 g (0.5 mmol) of T9-PhPCu(II) is dissolved in 150 mL of chloroform, to which 5.3 mL (100 mmol) of Br$_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.4142 g of dark green solids, T9-PhPBr$_8$Cu(II), with a yield 48.5%; in a 250 mL single-neck round-bottom flask, 0.3416 g (0.2 mmol) of T9-PhPBr$_8$Cu(II) is dissolved in 100 mL of chloroform, to which 15 mL (180 mmol) of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2410 g of dark green solids, T9-PhPBr$_8$, with a yield of 73.1%; in a 1 L single-neck round-bottom flask, 0.1652 g (0.1 mmol) of T9-PhPBr$_8$ is dissolved in 50 mL of chloroform, to which 0.1771 g (10 mmol) of anhydrous cobalt(II) acetate (dissolved in 500 mL of methanol) is added, stirred at 75° C. for 12.0 h, and washed with distilled water (5×200 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1177 g of reddish brown solids, T9-PhPBr$_8$Co(II), with a yield of is 69.1%.

Example 7

In a 500 mL three-neck round-bottom flask, 20.6241 g (100 mmol) of 9-formaldehyde phenanthrene is dissolved in 300 mL of propionic acid, stirred and heated to reflux for 10 min under the protection of N$_2$; 6.7812 g (100 mmol) of freshly distilled pyrrole is added dropwise, reacted for 2.0 h, cooled to room temperature, filtered with suction, recrystallized with methanol, and dried to obtain 5.0710 g of porphyrin T9-PhP, with a yield of 20%; in a 250 mL single-neck round-bottom flask, 1.0152 g (1.0 mmol) of T9-PhP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.8858 g of T9-PhPCu(II), with a yield of 80%; in a 500 mL single-neck round-bottom flask, 0.5401 g (0.5 mmol) of T9-PhPCu(II) is dissolved in 150 mL of chloroform, to which 5.3 mL (100 mmol) of Br$_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.4142 g of dark green solids, T9-PhPBr$_8$Cu(II), with a yield 48.5%; in a 250 mL single-neck round-bottom flask, 0.3416 g (0.2 mmol) of T9-PhPBr$_8$Cu(II) is dissolved in 100 mL of chloroform, to which 15 mL (180 mmol) of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2410 g of dark green solids, T9-PhPBr$_8$, with a yield of 73.1%; in a 250 mL single-neck round-bottom flask, 0.1652 g (0.1 mmol) of T9-PhPBr$_8$ is dissolved in 50 mL of chloroform, to which 0.0885 g (0.5 mmol) of anhydrous cobalt(II) acetate (dissolved in 25 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1114 g of reddish brown solids, T9-PhPBr$_8$Co(II), with a yield of is 65.4%.

Example 8

In a 500 mL three-neck round-bottom flask, 23.0260 g (100 mmol) 1-pyrene formaldehyde is dissolved in 300 mL of propionic acid, stirred and heated to reflux for 10 min under the protection of N$_2$; 6.7812 g (100 mmol) of freshly distilled pyrrole is added dropwise, reacted for 2.0 h, cooled to room temperature, filtered with suction, recrystallized with methanol, and dried to obtain 5.5566 g of porphyrin T1-PyP, with a yield of 20%; in a 250 mL single-neck round-bottom flask, 1.1113 g (1.0 mmol) of T1-PyP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.9383 g of T1-PyPCu(II), with a yield of 80%; in a 500 mL single-neck round-bottom flask, 0.5864 g (0.5 mmol) of T1-PyPCu(II) is dissolved in 150 mL of chloroform, to which 5.3 mL (100 mmol) of $Br_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.4257 g of dark green solids, T1-PyPBr$_8$Cu(II), with a yield 47.2%; in a 250 mL single-neck round-bottom flask, 0.3610 g (0.2 mmol) of T1-PyPBr$_8$Cu(II) is dissolved in 100 mL of chloroform, to which 15 mL (180 mmol) of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2485 g of dark green solids, T1-PyPBr$_8$, with a yield of 71.3%; in a 250 mL single-neck round-bottom flask, 0.1742 g (0.1 mmol) of T1-PyPBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1260 g of reddish brown solids, T1-PyPBr$_8$Co(II), with a yield of is 70.1%.

Example 9

In a 500 mL three-neck round-bottom flask, 23.0260 g (100 mmol) 1-pyrene formaldehyde is dissolved in 300 mL of propionic acid, stirred and heated to reflux for 10 min under the protection of $N_2$; 6.7812 g (100 mmol) of freshly distilled pyrrole is added dropwise, reacted for 2.0 h, cooled to room temperature, filtered with suction, recrystallized with methanol, and dried to obtain 5.5566 g of porphyrin T1-PyP, with a yield of 20%; in a 250 mL single-neck round-bottom flask, 1.1113 g (1.0 mmol) of T1-PyP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.9383 g of T1-PyPCu(II), with a yield of 80%; in a 500 mL single-neck round-bottom flask, 0.5864 g (0.5 mmol) of T1-PyPCu(II) is dissolved in 150 mL of chloroform, to which 0.3 mL (5 mmol) of $Br_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.3752 g of dark green solids, T1-PyPBr$_8$Cu(II), with a yield 41.6%; in a 250 mL single-neck round-bottom flask, 0.3610 g (0.2 mmol) of T1-PyPBr$_8$Cu(II) is dissolved in 100 mL of chloroform, to which 15 mL (180 mmol) of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2485 g of dark green solids, T1-PyPBr$_8$, with a yield of 71.3%; in a 250 mL single-neck round-bottom flask, 0.1742 g (0.1 mmol) of T1-PyPBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1260 g of reddish brown solids, T1-PyPBr$_8$Co(II), with a yield of is 70.1%.

Example 10

In a 500 mL three-neck round-bottom flask, 23.0260 g (100 mmol) 1-pyrene formaldehyde is dissolved in 300 mL of propionic acid, stirred and heated to reflux for 10 min under the protection of $N_2$; 6.7812 g (100 mmol) of freshly distilled pyrrole is added dropwise, reacted for 2.0 h, cooled to room temperature, filtered with suction, recrystallized with methanol, and dried to obtain 5.5566 g of porphyrin T1-PyP, with a yield of 20%; in a 250 mL single-neck round-bottom flask, 1.1113 g (1.0 mmol) of T1-PyP is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.9383 g of T1-PyPCu(II), with a yield of 80%; in a 500 mL single-neck round-bottom flask, 0.5864 g (0.5 mmol) of T1-PyPCu(II) is dissolved in 150 mL of chloroform, to which 13.3 mL (250 mmol) of $Br_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.5114 g of dark green solids, T1-PyPBr$_8$Cu(II), with a yield 56.7%; in a 250 mL single-neck round-bottom flask, 0.3610 g (0.2 mmol) of T1-PyPBr$_8$Cu(II) is dissolved in 100 mL of chloroform, to which 15 mL (180 mmol) of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2485 g of dark green solids, T1-PyPBr$_8$, with a yield of 71.3%; in a 250 mL single-neck round-bottom flask, 0.1742 g (0.1 mmol) of T1-PyPBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1260 g of reddish brown solids, T1-PyPBr$_8$Co(II), with a yield of is 70.1%.

Example 11

In a 500 mL three-neck round-bottom flask, 28.234 g (100 mmol) of p-(9-anthracene) benzaldehyde is dissolved in 300 mL of propionic acid, stirred and heated to reflux for 10 min under the protection of N$_2$; 6.7812 g (100 mmol) of freshly distilled pyrrole is added dropwise, reacted for 2.0 h, cooled to room temperature, filtered with suction, recrystallized with methanol, and dried to obtain 6.2682 g of porphyrin T[4-(9-An)P]P, with a yield of 19%; in a 250 mL single-neck round-bottom flask, 1.3192 g (1.0 mmol) of T[4-(9-An)P]P is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.9940 g of T[4-(9-An)P]PCu(II), with a yield of 72%; in a 500 mL single-neck round-bottom flask, 0.6911 g (0.5 mmol) of T[4-(9-An)P]PCu(II) is dissolved in 150 mL of chloroform, to which 13.3 mL (250 mmol) of Br$_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.5413 g of dark green solids, T[4-(9-An)P]PBr$_8$Cu(II), with a yield 53.8%; in a 250 mL single-neck round-bottom flask, 0.4025 g (0.2 mmol) of T[4-(9-An)P]PBr$_8$Cu(II) is dissolved in 100 mL of chloroform, to which 15 mL (180 mmol) of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2981 g of dark green solids, T[4-(9-An)P]PBr$_8$, with a yield of 76.4%; in a 250 mL single-neck round-bottom flask, 0.1951 g (0.1 mmol) of T[4-(9-An)P]PBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1373 g of reddish brown solids, T[4-(9-An)P]PBr$_8$Co(II), with a yield of is 68.4%.

Example 12

In a 500 mL three-neck round-bottom flask, 28.234 g (100 mmol) of p-(9-anthracene) benzaldehyde is dissolved in 300 mL of propionic acid, stirred and heated to reflux for 10 min under the protection of N$_2$; 6.7812 g (100 mmol) of freshly distilled pyrrole is added dropwise, reacted for 2.0 h, cooled to room temperature, filtered with suction, recrystallized with methanol, and dried to obtain 6.2682 g of porphyrin T[4-(9-An)P]P, with a yield of 19%; in a 250 mL single-neck round-bottom flask, 1.3192 g (1.0 mmol) of T[4-(9-An)P]P is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.9940 g of T[4-(9-An)P]PCu(II), with a yield of 72%; in a 500 mL single-neck round-bottom flask, 0.6911 g (0.5 mmol) of T[4-(9-An)P]PCu(II) is dissolved in 150 mL of chloroform, to which 0.3 mL (5 mmol) of Br$_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.4104 g of dark green solids, T[4-(9-An)P]PBr$_8$Cu(II), with a yield 45.5%; in a 250 mL single-neck round-bottom flask, 0.4025 g (0.2 mmol) of T[4-(9-An)P]PBr$_8$Cu(II) is dissolved in 100 mL of chloroform, to which 15 mL (180 mmol) of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2981 g of dark green solids, T[4-(9-An)P]PBr$_8$, with a yield of 76.4%; in a 250 mL single-neck round-bottom flask, 0.1951 g (0.1 mmol) of T[4-(9-An)P]PBr$_8$ is dissolved in 50 mL of chloroform, to which 0.1771 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1373 g of reddish brown solids, T[4-(9-An)P]PBr$_8$Co(II), with a yield of is 68.4%.

Example 13

In a 500 mL three-neck round-bottom flask, 28.234 g (100 mmol) of p-(9-anthracene) benzaldehyde is dissolved in 300 mL of propionic acid, stirred and heated to reflux for 10 min under the protection of N$_2$; 6.7812 g (100 mmol) of freshly distilled pyrrole is added dropwise, reacted for 2.0 h, cooled to room temperature, filtered with suction, recrystallized with methanol, and dried to obtain 6.2682 g of porphyrin T[4-(9-An)P]P, with a yield of 19%; in a 250 mL single-neck round-bottom flask, 1.3192 g (1.0 mmol) of T[4-(9-An)P]P is dissolved in 100 mL of chloroform, to which 1.9965 g (10 mmol) of methanol solution of anhydrous copper(II) acetate is added, refluxed for 3.0 h, cooled to room temperature, filtered with suction, and dried to obtain 0.9940 g of T[4-(9-An)P]PCu(II), with a yield of 72%; in a 500 mL single-neck round-bottom flask, 0.6911 g (0.5 mmol) of T[4-(9-An)P]PCu(II) is dissolved in 150 mL of chloroform, to which 13.3 mL (250 mmol) of Br$_2$ is titrated at constant pressure, stirred at room temperature for 24.0 h, quenched with the addition of 3.160 g (20 mmol) of sodium thiosulfate (dissolved in 100 mL of distilled water), and stirred at room temperature for 1.0 h. Washing is performed with distilled water (5×100 mL) to afford an organic phase in the lower layer which is a dark green solution, and which is dried over anhydrous sodium sulfate for 30 min, filtered with suction, and desolventized under reduced pressure to obtain 0.5718 g of dark green solids, T[4-(9-An)P]PBr$_8$Cu(II), with a yield 63.4%; in a 250 mL single-neck round-bottom flask, 0.4025 g (0.2 mmol) of T[4-(9-An)P]PBr$_8$Cu(II) is dissolved in 100 mL of chloroform, to which 15 mL (180 mmol) of perchloric acid is added, stirred at room temperature for 12.0 h, and washed with a saturated sodium bicarbonate solution (5×100 mL) to afford an organic phase in the lower layer which is a dark green solution, and which is dried over anhydrous sodium sulfate, filtered with suction, and desolventized under reduced pressure to obtain 0.2981 g of dark green solids, T[4-(9-An)P]PBr$_8$, with a yield of 76.4%; in a 250 mL single-neck round-bottom flask, 0.1951 g (0.1 mmol) of T[4-(9-An)P]PBr$_8$ is dissolved in 50 mL of chloroform, to which 0.1951 g (1 mmol) of anhydrous cobalt(II) acetate (dissolved in 50 mL of methanol) is added, stirred at 75° C. for 12.0 h, and washed with distilled water (5×100 mL) to afford an organic phase in the lower layer which is a reddish brown solution, and which is dried over anhydrous sodium sulfate for 30 min, filtered with suction, and desolventized under reduced pressure; the product is vacuum-dried at 60° C. for 3.0 h to obtain 0.1373 g of reddish brown solids, T[4-(9-An)P]PBr$_8$Co(II), with a yield of is 68.4%.

Example 14

In a 100 mL stainless steel autoclave with a polytetrafluoroethylene liner, 0.0003 g (0.00020 mmol) of 5,10,15,20-tetra(9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.38%, selectivity of cyclohexanol is 45%, selectivity of cyclohexanone is 40%, selectivity of cyclohexyl hydroperoxide is 12%, and selectivity of adipic acid is 3%, without detecting formation of glutaric acid.

Example 15

In a 100 mL stainless steel autoclave with a polytetrafluoroethylene liner, 0.0034 g (0.0020 mmol) of 5,10,15,20-tetra(9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.49%, selectivity of cyclohexanol is 45%, selectivity of cyclohexanone is 42%, selectivity of cyclohexyl hydroperoxide is 10%, and selectivity of adipic acid is 3%, without detecting formation of glutaric acid.

Example 16

In a 100 mL stainless steel autoclave with a polytetrafluoroethylene liner, 0.0051 g (0.0030 mmol) of 5,10,15,20-tetra(9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.63%, selectivity of cyclohexanol is 47%, selectivity of cyclohexanone is 39%, selectivity of cyclohexyl hydroperoxide is 11%, and selectivity of adipic acid is 3%, without detecting formation of glutaric acid.

Example 17

In a 100 mL stainless steel autoclave with a polytetrafluoroethylene liner, 0.3400 g (0.2000 mmol) of 5,10,15,20-tetra(9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.69%, selectivity of cyclohexanol is 46%, selectivity of cyclohexanone is 40%, selectivity of cyclohexyl hydroperoxide is 10%, and selectivity of adipic acid is 4%, without detecting formation of glutaric acid.

Example 18

In a 100 mL stainless steel autoclave with a polytetrafluoroethylene liner, 0.3400 g (0.0030 mmol) of 5,10,15,20-tetra(9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 600 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.28%, selectivity of cyclohexanol is 40%, selectivity of cyclohexanone is 38%, selectivity of cyclohexyl hydroperoxide is 15%, and selectivity of adipic acid is 7%, without detecting formation of glutaric acid.

Example 19

In a 100 mL stainless steel autoclave with a polytetrafluoroethylene liner, 0.3400 g (0.0030 mmol) of 5,10,15,20-tetra (9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 1200 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.75%, selectivity of cyclohexanol is 46%, selectivity of cyclohexanone is 42%, selectivity of cyclohexyl hydroperoxide is 9%, and selectivity of adipic acid is 3%, without detecting formation of glutaric acid.

Example 20

In a 100 mL stainless steel autoclave with a polytetrafluoroethylene liner, 0.0051 g (0.0030 mmol) of 5,10,15,20-tetra (9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 0.2 MPa. The reaction is carried out with stirring at 120° C., 0.2 MPa oxygen pressure, 800 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.20%, selectivity of cyclohexanol is 39%, selectivity of cyclohexanone is 30%, selectivity of cyclohexyl hydroperoxide is 25%, and selectivity of adipic acid is 6%, without detecting formation of glutaric acid.

Example 21

In a 100 mL stainless steel autoclave with a polytetrafluoroethylene liner, 0.0051 g (0.0030 mmol) of 5,10,15,20-tetra (9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 3 MPa. The reaction is carried out with stirring at 120° C., 3 MPa oxygen pressure, 800 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.61%, selectivity of cyclohexanol is 45%, selectivity of cyclohexanone is 37%, selectivity of cyclohexyl hydroperoxide is 13%, and selectivity of adipic acid is 5%, without detecting formation of glutaric acid.

Example 22

In a 100 mL stainless steel autoclave with a polytetrafluoroethylene liner, 0.0051 g (0.0030 mmol) of 5,10,15,20-tetra (9-phenanthryl)-2,3,7,8,12,13,17,18-octabromoporphyrin cobalt(II) is dispersed in 16.8320 g (200 mmol) of cyclohexane; the autoclave is sealed, and heated to 100° C. with stirring, to which oxygen is introduced to 1.0 MPa. The reaction is carried out with stirring at 100° C., 1.0 MPa oxygen pressure, 800 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 4.12%, selectivity of cyclohexanol is 40%, selectivity of cyclohexanone is 38%, selectivity of cyclohexyl hydroperoxide is 20%, and selectivity of adipic acid is 2%, without detecting formation of glutaric acid.

Example 23

In a 100 mL stainless steel autoclave with a polytetrafluoroethylene liner, 0.0051 g (0.0030 mmol) of 5,10,15,20-tetra (9-phenanthryl)-2,3,7,8,12,13,17,18-octabromoporphyrin cobalt(II) is dispersed in 16.8320 g (200 mmol) of cyclohexane; the autoclave is sealed, and heated to 130° C. with stirring, to which oxygen is introduced to 1.0 MPa. The reaction is carried out with stirring at 130° C., 1.0 MPa oxygen pressure, 800 rpm for 8.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 6.12%, selectivity of cyclohexanol is 46%, selectivity of cyclohexanone is 36%, selectivity of cyclohexyl hydroperoxide is 8%, and selectivity of adipic acid is 10%, without detecting formation of glutaric acid.

Example 24

In a 100 mL stainless steel autoclave with a polytetrafluoroethylene liner, 0.0003 g (0.00020 mmol) of 5,10,15,20-tetra(9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 3.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 3.75%, selectivity of cyclohexanol is 35%, selectivity of cyclohexanone is 28%, selectivity of cyclohexyl hydroperoxide is 35%, and selectivity of adipic acid is 2%, without detecting formation of glutaric acid.

Example 25

In a 100 mL stainless steel autoclave with a polytetrafluoroethylene liner, 0.0003 g (0.00020 mmol) of 5,10,15,20-tetra(9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 12.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 7.35%, selectivity of cyclohexanol is 43%, selectivity of cyclohexanone is 33%, selectivity of cyclohexyl hydroperoxide is 10%, and selectivity of adipic acid is 14%, without detecting formation of glutaric acid.

Example 26

In a 100 mL stainless steel autoclave with a polytetrafluoroethylene liner, 0.0003 g (0.00020 mmol) of 5,10,15,20-tetra(9-phenanthryl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 24.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 10.34%, selectivity of cyclohexanol is 42%, selectivity of cyclohexanone is 31%, selectivity of cyclohexyl hydroperoxide is 10%, and selectivity of adipic acid is 17%, without detecting formation of glutaric acid.

Example 27

In a 100 mL stainless steel autoclave with a polytetrafluoroethylene liner, 0.0002 g (0.00020 mmol) of 5,10,15,20-tetra(1-pyrenyl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.64%, selectivity of cyclohexanol is 47%, selectivity of cyclohexanone is 39%, selectivity of cyclohexyl hydroperoxide is 11%, and selectivity of adipic acid is 3%, without detecting formation of glutaric acid.

Example 28

In a 100 mL stainless steel autoclave with a polytetrafluoroethylene liner, 0.0023 g (0.0020 mmol) of 5,10,15,20-tetra(1-pyrenyl)-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.73%, selectivity of cyclohexanol is 48%, selectivity of cyclohexanone is 38%, selectivity of cyclohexyl hydroperoxide is 12%, and selectivity of adipic acid is 2%, without detecting formation of glutaric acid.

Example 29

In a 100 mL stainless steel autoclave with a polytetrafluoroethylene liner, 0.0035 g (0.0030 mmol) of 5,10,15,20-tetra(1-pyrenyl)-2,3,7,8,12,13,17,18-octabromoporphyrin cobalt (II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.84%, selectivity of cyclohexanol is 49%, selectivity of cyclohexanone is 37%, selectivity of cyclohexyl hydroperoxide is 12%, and selectivity of adipic acid is 2%, without detecting formation of glutaric acid.

Example 30

In a 100 mL stainless steel autoclave with a polytetrafluoroethylene liner, 0.0004 g (0.00020 mmol) of 5,10,15,20-tetra[4-(9-anthryl)-phenyl)]-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 5.98%, selectivity of cyclohexanol is 51%, selectivity of cyclohexanone is 37%, selectivity of cyclohexyl hydroperoxide is 9%, and selectivity of adipic acid is 3%, without detecting formation of glutaric acid.

Example 31

In a 100 mL stainless steel autoclave with a polytetrafluoroethylene liner, 0.0040 g (0.0020 mmol) of 5,10,15,20-tetra[4-(9-anthryl)-phenyl)]-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 6.25%, selectivity of cyclohexanol is 52%, selectivity of cyclohexanone is 36%, selectivity of cyclohexyl hydroperoxide is 10%, and selectivity of adipic acid is 2%, without detecting formation of glutaric acid.

Example 32

In a 100 mL stainless steel autoclave with a polytetrafluoroethylene liner, 0.0060 g (0.0030 mmol) of 5,10,15,20-tetra[4-(9-anthryl)-phenyl)]-2,3,7,8,12,13,17,18-octabromoporphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 6.34%, selectivity of cyclohexanol is 54%, selectivity of cyclohexanone is 35%, selectivity of cyclohexyl hydroperoxide is 9%, and selectivity of adipic acid is 2%, without detecting formation of glutaric acid.

Example 33

In a 100 mL stainless steel autoclave with a polytetrafluoroethylene liner, 0.0003 g (0.00020 mmol) of 5,10,15,20-tetra(9-phenanthryl)-2,3,7,8,12,13,17,18-octabromoporphyrin cobalt(II) is dispersed in 14.0260 g (200 mmol) of cyclopentane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine ($PPh_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclopentane is 3.7%, selectivity of cyclopentanol is 47%, selectivity of cyclopentanone is 34%, selectivity of cyclopentyl hydroperoxide is 16%, and selectivity of glutaric acid is 3%, without detecting formation of succinic acid.

Example 34

In a 100 mL stainless steel autoclave with a polytetrafluoroethylene liner, 0.0003 g (0.00020 mmol) of 5,10,15,20-tetra(9-phenanthryl)-2,3,7,8,12,13,17,18-octabromoporphyrin cobalt(II) is dispersed in 19.6381 g (200 mmol) of cycloheptane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 13.1145 g (50.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cycloheptane is 27.1%, selectivity of cycloheptanol is 45%, selectivity of cycloheptanone is 33%, selectivity of cycloheptyl hydroperoxide is 22%, without detecting formation of pimelic acid and adipic acid.

Example 35

In a 100 mL stainless steel autoclave with a polytetrafluoroethylene liner, 0.0003 g (0.00020 mmol) of 5,10,15,20-tetra(9-phenanthryl)-2,3,7,8,12,13,17,18-octabromoporphyrin cobalt(II) is dispersed in 22.4440 g (200 mmol) of cyclooctane; the autoclave is sealed, and heated to 120° C. with stirring, to which oxygen is introduced to 1.0 MPa. The reaction is carried out with stirring at 110° C., 1.0 MPa oxygen pressure, 800 rpm for 8.0 h. After the completion of reaction, the reaction mixture is cooled with ice water to room temperature; 13.1145 g (50.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclooctane is 40.5%, selectivity of cyclooctanol is 31%, selectivity of cyclooctanone is 25%, selectivity of cyclooctyl hydroperoxide is 23%, without detecting formation of suberic acid and pimelic acid.

Example 36

In a 100 mL stainless steel autoclave with a polytetrafluoroethylene liner, 0.0003 g (0.00020 mmol) of 5,10,15,20-tetra(9-phenanthryl)-2,3,7,8,12,13,17,18-octabromoporphyrin cobalt(II) is dispersed in 33.6641 g (200 mmol) of cyclododecane; the autoclave is sealed, and heated to 120° C. with stirring, to which oxygen is introduced to 1.0 MPa. The reaction is carried out with stirring at 110° C., 1.0 MPa oxygen pressure, 800 rpm for 8.0 h. After the completion of reaction, the reaction mixture is cooled with ice water to room temperature; 13.1145 g (50.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclododecane is 42.6%, selectivity of cyclododecanol is 41%, selectivity of cyclododecanone is 31%, selectivity of cyclododecanyl hydroperoxide is 28%, without detecting formation of dodecanedioic acid and undecanedioic acid.

Example 37 (Comparative Experiment)

In a 100 mL stainless steel autoclave with a polytetrafluoroethylene liner, 0.0024 g (0.0030 mmol) of 5,10,15,20-tetra(4-chlorophenyl)porphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 3.78%, selectivity of cyclohexanol is 32%, selectivity of cyclohexanone is 38%, selectivity of cyclohexyl hydroperoxide is 15%, selectivity of adipic acid is 12%, and selectivity of glutaric acid is 3%.

Example 38 (Comparative Experiment)

In a 100 mL stainless steel autoclave with a polytetrafluoroethylene liner, 0.0031 g (0.0030 mmol) of 5,10,15,20-tetra(2,3,4,5,6-pentafluorophenyl)porphyrin cobalt(II) is dispersed in 16.8320 g (200 mmol) of cyclohexane; the autoclave is sealed, and heated to 120° C. with stirring, to which oxygen is introduced to 1.0 MPa. The reaction is carried out with stirring at 120° C., 1.0 MPa oxygen pressure, 800 rpm for 8.0 h. After the completion of reaction, the reaction mixture is cooled with ice water to room temperature; 1.3115 g (5.00 mmol) of triphenylphosphine (PPh$_3$) is added to the reaction mixture, and stirred at room temperature for 30 min to reduce the generated peroxides. The volume of the resulting reaction mixture is set to be 100 mL by using acetone as the solvent. 10 mL of the resulting solution is pipetted for gas chromatography analysis using toluene as the internal standard; 10 mL of the resulting solution is pipetted for liquid chromatography analysis using benzoic acid as the internal standard. The conversion of cyclohexane is 4.12%, selectivity of cyclohexanol is 24%, selectivity of cyclohexanone is 46%, selectivity of cyclohexyl hydroperoxide is 17%, selectivity of adipic acid is 11%, and selectivity of glutaric acid is 2%.

Example 39 (Scale-Up Experiment)

In a 1 L stainless steel autoclave with a polytetrafluoroethylene liner, 0.0034 g (0.0020 mmol) of 5,10,15,20-tetra (9-phenanthryl)-2,3,7,8,12,13,17,18-octabromoporphyrin cobalt(II) is dispersed in 168.320 g (2.00 mol) of cyclohexane; the autoclave is sealed, and heated to 120° C. with stirring, to which oxygen is introduced to 1.0 MPa. The reaction is carried out with stirring at 120° C., 1.0 MPa oxygen pressure, 600 rpm for 12.0 h. After the completion of reaction, the reaction mixture is cooled with ice water to room temperature; 13.1145 g (50.00 mmol) of triphenylphosphine (PPh$_3$) is added to the reaction mixture, and stirred at room temperature for 30 min to reduce the generated peroxides. Distillation is performed to recover 157.03 g of cyclohexane, with a conversion of 6.71%; distillation is performed under reduced pressure to obtain 6.410 g of cyclohexanol with a selectivity of 48% and 6.08 g of cyclohexanone with a selectivity of 46%.

What is claimed is:

1. A confined porphyrin Co(II) having a structure as shown in formula (I):

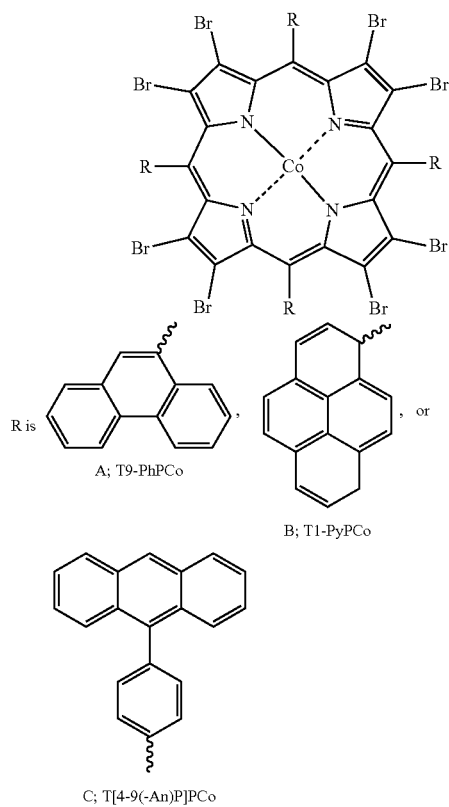

2. A method for preparing the confined porphyrin Co(II) according to claim 1, wherein the preparation method is as follows:
    equimolar amounts of an aromatic aldehyde and a pyrrole are condensed under acidic conditions to synthesize a phenyl porphyrin compound;
    the porphyrin compound is dissolved in chloroform, to which a methanol solution of anhydrous copper (II) acetate is added, stirred at reflux for 3.0-8.0 h, cooled to room temperature, and filtered with suction to afford a mother liquor, which is desolventized under reduced pressure to obtain a porphyrin Cu(II);
    the porphyrin Cu(II) is dissolved in chloroform, to which liquid bromine is added dropwise and stirred at room temperature for 24.0-36.0 h, which is quenched with a saturated sodium thiosulfate solution after the completion of reaction, wherein liquid separation is performed by extraction with chloroform and water, and the organic phase in the lower layer is dried over anhydrous sodium sulfate, filtered with suction, and desolventized under reduced pressure to obtain a confined brominated porphyrin Cu(II);
    the confined brominated porphyrin Cu(II) is dissolved in chloroform, to which perchloric acid is added and stirred at room temperature for 12.0-24.0 h, and neutralized with a saturated sodium bicarbonate solution, wherein liquid separation is performed by extraction with chloroform and water, and the organic phase in the lower layer is dried over anhydrous sodium sulfate, filtered with suction, and desolventized under reduced pressure to obtain a brominated porphyrin; and
    the brominated porphyrin is dissolved in chloroform, to which a methanol solution of anhydrous cobalt(II) acetate is added and stirred at reflux for 12.0-24.0 h, wherein liquid separation is performed by extraction with chloroform and water, and the organic phase in the lower layer is dried over anhydrous sodium sulfate, filtered with suction, desolventized under reduced pressure, and vacuum-dried at 60 to 150° C. for 8.0 to 36.0 h to obtain the confined porphyrin Co(II).

3. The method for preparing the confined porphyrin Co(II) according to claim 2, wherein the ratio of the amount of substance of porphyrin Cu(II) to liquid bromine is 1:(500 to 10).

4. The method for preparing the confined porphyrin Co(II) according to claim 2, wherein the ratio of the amount of substance of the confined porphyrin Cu(II) to perchloric acid is 1:(2000 to 200).

5. The method for preparing the confined porphyrin Co(II) according to claim 2, wherein the ratio of the amount of substance of the confined porphyrin to anhydrous cobalt(II) acetate is 1:(100 to 5).

6. A method for the catalytic oxidation of cycloalkanes comprising the following process steps: the confined porphyrin Co(II) according to claim 1 is dispersed in cycloalkanes; the reaction system is sealed, and heated to 100 to 130° C. with stirring; oxygen is introduced to 0.2 to 3.0 MPa; the reaction is carried out for 3 to 24 h with stirring with the set temperature and oxygen pressure being maintained; and then the reaction solution is subjected to post-treatment to obtain the products cycloalkanols and cycloalkanones.

7. The method according to claim 6, wherein the ratio of the amount of substance of the porphyrin Co(II) to cycloalkane is 1:(100000 to 1000); the stirring rate is 600 to 1200 rpm; the reaction temperature is 100 to 130° C.; the reaction pressure is 0.2 to 3.0 MPa; the reaction time is 3.0 to 24.0 h.

8. The method according to claim 6, wherein the confined porphyrin Co(II) is selected from the compounds represented by formula (I), or a mixture of two or more thereof in a random ratio, and the compounds are A: 5,10,15,20-tetra(9-phenanthryl)-2,3,7,8,12,13,17,18-octabromoporphyrin cobalt(II), B: 5,10,15,20-tetra(1-pyrenyl)-2,3,7,8,12,13,17,18-octabromoporphyrin cobalt(II), and C: 5,10,15,20-tetra[4-(9-anthryl)-phenyl]-2,3,7,8,12,13,17,18-octabromoporphyrin cobalt(II), respectively.

9. The method according to claim 6, wherein the oxidant is oxygen, air or a mixture thereof in a random ratio.

* * * * *